(12) United States Patent
Robin

(10) Patent No.: US 10,138,290 B2
(45) Date of Patent: Nov. 27, 2018

(54) PROCESS FOR PROTEIN PRODUCTION

(75) Inventor: Jarno Robin, Skovlunde (DK)

(73) Assignee: Novo Nordisk Healthcare AG, Zurich (CH)

( * ) Notice: Subject to any disclaimer, the term of this patent is extended or adjusted under 35 U.S.C. 154(b) by 57 days.

(21) Appl. No.: 13/823,847

(22) PCT Filed: Oct. 5, 2011

(86) PCT No.: PCT/EP2011/067372
§ 371 (c)(1),
(2), (4) Date: May 30, 2013

(87) PCT Pub. No.: WO2012/045769
PCT Pub. Date: Apr. 12, 2012

(65) Prior Publication Data
US 2013/0244283 A1 Sep. 19, 2013

Related U.S. Application Data

(60) Provisional application No. 61/392,713, filed on Oct. 13, 2010.

(30) Foreign Application Priority Data

Oct. 5, 2010 (EP) ..................................... 10186545

(51) Int. Cl.
C07K 14/755 (2006.01)
C12N 9/64 (2006.01)

(52) U.S. Cl.
CPC ............ *C07K 14/755* (2013.01); *C12N 9/644* (2013.01); *C12N 9/6424* (2013.01); *C12N 9/6437* (2013.01)

(58) Field of Classification Search
None
See application file for complete search history.

(56) References Cited

U.S. PATENT DOCUMENTS

| | | | |
|---|---|---|---|
| 4,770,999 A | | 9/1988 | Kaufman et al. |
| 4,956,080 A | * | 9/1990 | Josefik .................. B01F 3/0446 210/109 |
| 6,544,424 B1 | | 4/2003 | Shevitz |
| 7,521,210 B2 | | 4/2009 | Knudsen |
| 2005/0227913 A1 | | 10/2005 | Balasubramanian et al. |
| 2006/0166915 A1 | | 7/2006 | Persson et al. |
| 2008/0131934 A1 | | 6/2008 | Crowley et al. |
| 2008/0182297 A1 | * | 7/2008 | Reiter .................. C12N 5/0682 435/71.1 |
| 2009/0130060 A1 | | 5/2009 | Weimer et al. |
| 2010/0120094 A1 | | 5/2010 | Johnsen et al. |

FOREIGN PATENT DOCUMENTS

| | | |
|---|---|---|
| EP | 1707634 A1 | 10/2006 |
| JP | H01101882 A | 4/1989 |
| JP | H0253483 A | 2/1990 |
| JP | 2000-510701 A | 8/2000 |
| JP | 2004511248 A | 4/2004 |
| JP | 2005-512524 A | 5/2005 |
| JP | 2006525015 A | 11/2006 |
| JP | 2009045019 A | 3/2009 |
| JP | 2009535019 A | 10/2009 |
| WO | 87/04187 A1 | 7/1987 |
| WO | 88/08035 A1 | 10/1988 |
| WO | 90/02175 A1 | 3/1990 |
| WO | 97/43436 A1 | 11/1997 |
| WO | 2004/000366 A1 | 12/2003 |
| WO | 2004/099396 A1 | 11/2004 |
| WO | 2005/095578 A1 | 10/2005 |
| WO | 2006/018204 A1 | 2/2006 |
| WO | 2008/006494 A1 | 1/2008 |
| WO | 2008/152075 A1 | 12/2008 |
| WO | 2009/130198 A2 | 10/2009 |
| WO | 2010/003759 A2 | 1/2010 |

OTHER PUBLICATIONS

Wurm, Florian M; "Production of recombinant protein therapeutics in cultivated mammalian cells" Nature Biotechnology, 22, 1393-1398, 2004.*
Marcel de Vocht, Intensification of a PER.C6-based recombinant Ad35 manufacturing process to prepare for commercial scale production,Journal Crucell, , Year 2008 pp. 1-50 Link:http://www.refinetech.com/media/downloads/crucell-marcel-de-vocht-tb-vaccine-manufacture.pdf.
"The ATF(tm) System—Low Shear Separation" Refine Technology Co. distributed by Adaptive Biosystems Ltd, 2000; 33 pages.
"Using the ATF(tm) System to Harvest a Bioreactor" Refine Technology, Co., 2000, www.refinetech.com; 1 page.
"Using the ATF(tm) System to Perfuse a Bioreactor Seed Vessel" Refine Technology, Co., 2000; www.refinetech.com; 1 page.
BioProcess International, 2009, Online Educational Series, "Perfusion! Jeopardy or the ultimate Advantage?", 43 pages.
Brochure from Refine Technology Co., "ATF System, Improve your bioprocess", Published in 2009 (see D22, which link "PDF file—Click to download" led to D18); 4 pages.
Chotteau, V et al "Study of a perfusion process of Chinese Hamster Ovary cells by ATF filtration in bioreactor" 21st ESACT Meeting Jun. 7-10, 2009 Dublin, Ireland; 1 page.
Compton, B et al "Use of perfusion technology on the rise" Genetic Engineering & Biotechnology New, Oct. 1, 2007 vol. 27 No. 17; accessed from http://www.genengnews.com/gen-articles/use-of-perfusion-technology-on-the-rise/2227/ on Aug. 16, 2016.
Furey J. "Scale-up of a Cell Culture Perfusion Process" Genetic Engineering News, Apr. 1, 2002 vol. 22 No. 7 pp. 62-63.

(Continued)

*Primary Examiner* — David W Berke-Schlessel
(74) *Attorney, Agent, or Firm* — Leon Y. Lum

(57) ABSTRACT

The present invention relates to a process for the production of a haemostasis protein by continuous perfusion culturing of a cell culture in suspension, said cell culture expressing said haemostasis protein into said culture suspension, wherein the cell culture flows across a filter module, which filter module leads to a harvest port, the filter module having a mesh size of from 0.1 to 2.9 μm allowing passage across of the haemostasis protein and wherein the flow across the filter module is an alternating tangential flow. The invention also relates to a protein produced by the process of the invention.

16 Claims, 5 Drawing Sheets

(56) References Cited

OTHER PUBLICATIONS

GE Healthcare—BioProcess Product Guide 2008/2009; 260 Pages.
Gray et al "Measurement of activated Factor IX in Factor IX concentrates: correlation with in vivo thrombogenicity" Thromb Haemost 1995 vol. 73 Issue 4 pp. 675-679.
Hetzel, C "Tangential and schonend separiert", P&A-kompendium 2009/2010, S. 20, pp. 72-74.
Konstantinov, K "The "Push-to-Low" Approach for Optimization of High-Density Perfusion Cultures of Animal Cells" Adv Biochem Engin/Biotechnol 2006 vol. 101 pp. 75-98.
Prasa, D et al "Determination of Activated Factor IX in Factor IX Concentrates with a Chromogenic Substrate" Thrombosis Research 1998 vol. 92 Issue 2 pp. 99-102.
Sartorius Stedim Biotech "Products and Solutions for the Biopharmaceutical Industry" 2010; 642 Pages.
Thermo Scientific Hyclone BPC(r)—Products and Capabilities 2008/2009; 67 pages.
Wayback machine capture May 22, 2010; www.refinetech.com/download-centre.php; 1 page.
Bleckwenn et al., "Production of Recombinant Proteins by Vaccinia Virus in a Microcarrier Based Mammalian Cell Perfusion Bioreactor," Biotechnology & Bioengineering, 2005, vol. 90, No. 6, pp. 663-674.
Seung-Chul Kim et al, "Effect of Transmembrane Pressure on Factor VIII Yield in ATF Perfusion Culture for the Production of Recombinant Human Factor VIII Co-Expressed with von Willebrand Factor", Cytotechnology, 2015, vol. 68, No. 5, pp. 1687-1696.
Bodeker et al, "The Manufacturing of the Recombinant Factor VIII, Kogenate", Transfusion Medicine Reviews, 1992, vol. 6, No. 4, pp. 256-260.
Westgate et al., "Approximation of Continuous Fermentation by Semicontinuous Cultures," Biotechnology and Bioengineering, 1990, vol. 35, pp. 437-453.
Chun et al., Cytotechnology, Stable Expression of Recombinant Human Coagulation Factor XIII in Protein-Free Suspension Culture of Chinese Hamster Ovary Cells, 2001, vol. 37, No. 3, pp. 179-187.
Jim Furey, Genetic Engineering News, Continuous Cell Culture Using the ATF System a New Way to Grow Suspension or Anchorage-Dependent Cells, 2000, vol. 20, No. 10, pp. 52-53.

* cited by examiner

PROCESS FOR PROTEIN PRODUCTION

CROSS-REFERENCE TO RELATED APPLICATIONS

This application is a 35 U.S.C. § 371 National Stage application of International Application PCT/EP2011/067372 (WO 2012/045769 A1), filed Oct. 5, 2011, which claimed priority of European Patent Application 10186545.9, filed Oct. 5, 2010; this application claims priority under 35 U.S.C. § 119 of U.S. Provisional Application 61/392,713; filed Oct. 13, 2010, all hereby incorporated by reference.

TECHNICAL FIELD OF THE INVENTION

The present invention relates to a process for the production of a haemostasis protein by continuous perfusion culturing of a cell culture in suspension, said cell culture expressing said haemostasis protein into said culture suspension, wherein the cell culture flows across a filter module, which filter module leads to a harvest port, the filter module having a mesh size of from 0.1 to 2.9 μm allowing passage across of the haemostasis protein and wherein the flow across the filter module is an alternating tangential flow. The invention also relates to a protein produced by the process of the invention.

BACKGROUND OF THE INVENTION

The haemostasis proteins are components of the coagulation cascade. Deficiencies in any one of these proteins range from health complications to life threatening diseases. Deficiencies of these proteins were initially remedied by supply of haemostasis proteins from animal sources.

Typically, recombinant haemostasis proteins have been produced by either a continuous perfusion fermentation process or a repeated batch fermentation process. These fermentation processes provide high quality products. However, there is a continuing need to provide processes which produce a higher quantity of product, without a decrease in quality standards. The present invention provides such a process.

SUMMARY OF THE INVENTION

Accordingly, the first aspect of the invention provides a process for the production of a haemostasis protein by continuous perfusion culturing of a cell culture in suspension, said cell culture expressing said haemostasis protein into said culture suspension, the cell culture flows across a filter module, which filter module leads to a harvest port, the filter module having a mesh size of from 0.1 to 2.9 μm allowing passage across of the haemostasis protein and wherein the flow across the filter module is an alternating tangential flow. The size of the mesh contained within the filter module allows passage across the filter module of the haemostasis protein, but not of the cells or cell debris.

The process of the first aspect of the invention allows the production of high quality haemostasis proteins at significantly higher titres than prior used processes.

Furthermore, the advantages of higher titre, without compromising growth, productivity and product quality is obtained from lab-scale fermentations (around 5 L) to large-scale fermentations (at least 500 L). The present invention enable the production of the desired proteins up to ten times higher quantity than the prior art processes, without compromising product quality.

The present invention enables careful control of processing parameters, enabling a process to be run at a certain cell density in order to provide a high quality product at high concentrations within the bioreactor physical characteristics.

DETAILED DESCRIPTION OF THE INVENTION

Figure 1:
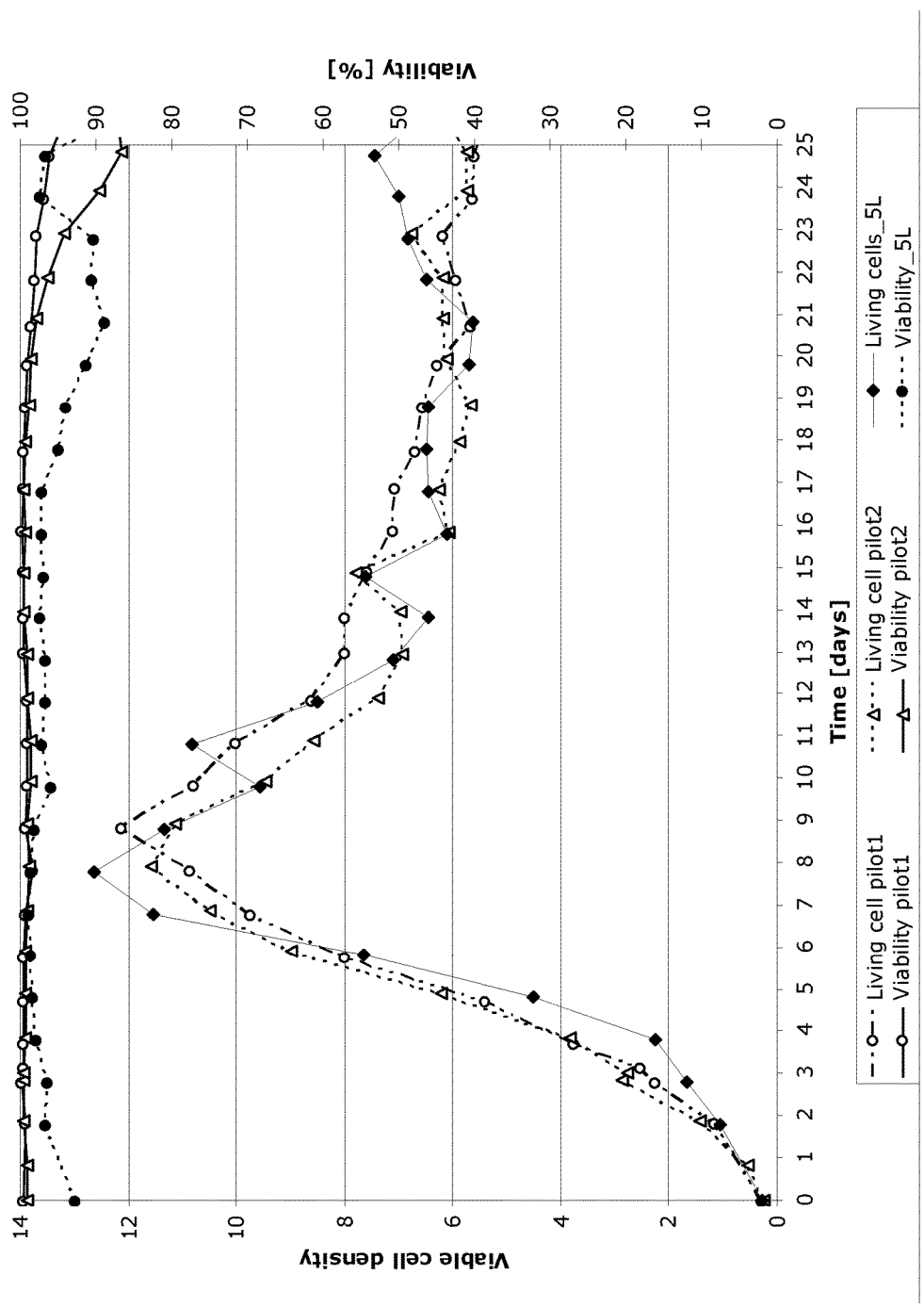
FIG. 1: Living cells concentration and viability for Factor IX at laboratory scale and pilot plant scale (>500 L) using ATF performed with bleed.

In the process of the invention, the haemostasis protein is preferably one of Factor VII (FVII), Factor VIII (FVIII) or Factor IX (FIX). There are numerous documents in the art which describe production of the haemostasis proteins, such as FVII, FVIII and FIX. The cell lines, cell culture and protein production technologies are well known and described in documents such as US 2006/0166915 and WO 2004/000366 for FVII, US 2009/0130060 and WO 2006/018204 for FVII and FIX, WO 2009/130198 and U.S. Pat. No. 4,770,999 for FIX and US 20100120094, WO 97/43436, WO 88/08035, WO 87/04187, WO 90/02175, US 20050227913 and EP 1707634 for FVIII. All of these documents are incorporated by reference and describe the well known principles of haemostasis protein production, which process steps can be used in accordance with the present invention. In order to produce the proteins recombinantly according to the invention, a cell line is used which expresses the protein (under appropriate conditions), when in culture. Such cell lines (with recombinant nucleic acid encoding a haemostasis protein such as FVII, FVIII or FIX) are known in the art, such as Baby Hamster Kidney cells (BHK), human cells, including immortalised human cells (e.g. PER.C6 cells), rat and mouse cells. According to the present invention, the cell culture is preferable a culture of a Chinese Hamster Ovary (CHO) cell line, which expresses the haemostasis protein of interest in culture. More preferable, the culture is the CHO-KI cell line.

The cell culture is present in suspension. Examples of medium useful for said culture and for the recombinant production of the protein of interest are well known. Suitable examples can be found in the prior art, including the patent filings described above and in the example section of this document.

The present invention is a continuous perfusion process to culture cells. The term perfusion process to culture cells has the convention meaning in the art, meaning that during culturing, cells are retained by a separation device; there is an outflow of liquid (from the culture) having a lower cell density than prior to separation and there is an inflow (to the culture) of cell culture medium. The present invention relates to the production of a desired protein. The clarified liquid harvested from the process has a concentration of the desired protein in the same range as does the cell culture. In the present invention it is preferable that at least one component of the cell culture medium is added continuously. Other components of the medium may be added continuously, semi-continuously or otherwise.

The separation device according to the present invention is a filter module. The filter module is preferably a hollow fibre filter in the form of a tubular membrane. Such filters/membranes are commonly known in the art, and can be obtained from, for example, General Electric (formerly Amersham). The filter is selected such that the mesh size is from 0.1 to 2.9 µm. This is a significant feature of the invention as this mesh size is selected to prevent, as far as possible, cell debris passing through the filter. Preferred filters for use according to the invention include those made of PS (polysulfone) or PES (polyethersulfone).

Alternating tangential flow (ATF) has been described since as long ago as the year 2000. An ATF system is generally composed of a diaphragm in addition to the filter (as described above), which filter can be connected to any type of bioreactor (stainless steel, glass, a single use bioreactor etc). By changing the pore size of the filter, the product produced can be either up-concentrated in the bioreactor or continuously removed. ATF means that there is alternating tangential flow occurring at the filter module, that is, there is one flow in the same direction as (i.e. tangential) to the membrane surfaces of the filter module and that there is another flow in a direction substantially perpendicular to said filter surface. Tangential flow can be obtained by methods known in the art, such as described in U.S. Pat. No. 6,544,424, the content of which is incorporated by reference.

The preferred bioreactor is a classical stirred bioreactor set-up with a bleed port, an ATF port (harvest port), a medium port, a base port, gas ports and additional ports for other additions.

It has not previously been thought that ATF can be used in a process to produce haemostasis proteins having, similar qualities to when produced in other processes (qualities like, for example GLA profile or activated form or glycol-profile or heavy chain), as material produced using other processes having a significantly lower yield, for example daily or volumetric production level or bulk product concentration.

The parameters of the system are generally those as described in the art. The pH, temperature, dissolved oxygen concentration, osmolarity of the cell culture medium are, in principle, not critical and depend on the cell chosen and product being produced. The parameters can be varied to maximise product quality and quantity. A balance is usually required. In accordance with the present invention, the perfusion rate is preferably from 0.7 to 10 volume per day, more preferably from 0.9 to 4 volume per day.

The process may be "bled" to remove unfiltered cell culture suspension in order to balance the volume of liquid being harvested and the volume of liquid being added to the culture. This bleed rate can be varied. The unfiltered liquid is preferably removed from the process at a rate of 0 to 0.2 volume per day (total volume of the process). The unfiltered cell culture suspension may be continuously removed from the process (continuous bleed). Alternatively, the unfiltered cell culture suspension may be removed discontinuously from the process (pulse bleed). With respect of Factor IX, a preferred bled rate is 0.01 to 0.2) volume per day (total volume of the process). This bleed is applied during the production phase in order to keep high cell viability as f.ex. above 80%".

The desired haemostasis protein is harvested from the system via the harvest port. It is most preferably purified in down-stream processing. Several down-stream processing steps may be combined. Typical downstream processing of the proteins of the invention are described in the art, such as those prior art including the patent filings referred to above. In the process of the invention, the liquid passing across the filter module contains the desired protein which is separated from the cells and cell debris in suspension culture by the passing the filter. This liquid is a clarified filtered suspension which contains the produced haemostasis protein. The filtered suspension is preferably harvested at a rate of from 0.7 to 10 volume per day (total volume of the process), preferably 0.7 to 1.0, or 0.8 to 1.4, or 1.0 to 1.2 volume per day.

The productivity of the process depends to some extent on the parameters of the process and otherwise depends on the cell clone exposing the haemostasis protein. The benefit of the present invention is the higher production compared to production in a non-ATF process using the same cell clone.

The cell viability at the start and during the process should be greater than 80%, preferably greater than 90%. The cell viability should be measured during the process and conditions adjusted as in all cultures if the cell viability drops below the desired level.

The cell density will vary. A suitable inoculum is in the range of $3\text{-}6\times10^5$ cells/ml.

The target cell density in the culture is below $80\times10^6$ cells/ml. A higher cell density produces a lower quantity and/or quality of product. In one preferred embodiment for FIX the cell density in the culture is below $8\times10^6$ cells/ml.

The temperature of the suspension is preferably maintained around 35.5 to 37.5° C., most preferably around 36.5° C. The pH of the suspension is preferably maintained around 6.95±0.45.

The dissolved oxygen concentration in the suspension is important. Preferably it is around 20 to 120% preferably around 30 to 70%, preferably around 45 to 55% preferably around 50%. Aeration may be achieved by any means. Typical and preferred means include aeration using a mixture of air and oxygen, preferably 100% oxygen through a sparger, while having constant airflow in the headspace.

In particular, the present invention relates to a process as set out in claim 1, for the production of Factor VII or Factor VIII or Factor IX protein.

A second aspect of the invention provides a FVII, FVIII or FIX protein produced by a process according to the first aspect of the invention. All preferred features of the first aspect also apply to the second aspect.

The quality of the protein can be measured according to criteria for that protein, since haemostasis proteins are known in the art. Measurement of FVII and FIX quality usually relates to the GLA profile (Gla10 to 12). Measurement of FVIII quality usually relates to the combined heavy and light claims.

EXAMPLES

Example 1

Example 1 describes the cultivation of Factor IX protein, performed using the process of the invention in an ATF perfusion device in a 5 L bioreactor (laboratory scale). The cultivation was carried out using an ATF perfusion device. The cultivation resulted in stable cell density, viability and product yield. The bleed range varied from 0 to 20%

Regarding the product quality, the activated FIX ("FIXa") is kept stable and low in the process. The GLA-profile (glutamic acid rich gamma-carboxyglutamic acid domain of FIX) regarding GLA 11&12 slightly decreased from 90-95% to 80-85% as the FIX concentration increases. The FIX yield reached is around 10 fold higher than the current prior art (non ATF) process used without compromising the product quality.

Strain Details

The cell type is a CHO-K1 strain expressing FIX.

Media:

The media used was a commercial media which supported the growth and production of the cells and product. Such media is usually supplemented with insulin, K1 vitamin, glutamine and glucose.

Process Overview

A process for FIX cultivation was followed to set up the ATF process according to the invention. The process involved thawing a cell bank vial and transfer of cells into T-flasks or shaker flask with low agitation (<30 rpm). Cell expansion was performed in shaker flasks until sufficient cells were produced in order to inoculate a 5 L bioreactor. At all process steps the cells are cultivated in suspension in serum free medium. In the bioreactor, the cultivation was performed in batch mode for the first 2-3 days. When the criteria for starting perfusion, pulse and harvest were met, the medium was supplied continuously. Glutamine and glucose were added by bolus or continuously (if required). The harvest was GMO-clarified by centrifugation and/or filtration and transferred to the primary recovery.

Bioreactor Parameters—Preparation and Test of 5 L Biostat B Plus

The pH electrode was calibrated with 4.0 and 7.4 buffers and checked with 7.0 buffer before assembling the tank. The tank was sterilized with PBS (9.6 g/l), which was later exchanged with medium. The oxygen electrode was calibrated with nitrogen (0%) and air (100%) in the PBS solution.

The pH electrode was eventually recalibrated to externally pH measurements. Tank, tubings and filters were tested for leaks.

Process Operating Conditions

The set points of the process parameter were adjusted as specified in the Table 1 below.

TABLE 1

Process operating condition for 5 L Biostat B plus

| Parameter | units | Set-point |
|---|---|---|
| Temperature | ° C. | 34-38) |
| pH | | 6.7-7.5 |
| DOT (dissolved oxygen tension) | % of air saturation | 10-90 |
| Stirring speed | rpm | 100-150 |
| Working volume | L | 4 |
| Base (sodium carbonate for pH control) | M | 1-3 |
| $CO_2$ (headspace) | NA | On demand |
| $O_2$ or air or mixture (sparging) | % | 0-100% |

Inoculation

The seeding cell concentration was targeted in the range: 3-6×10$^5$ cells/ml). The base was connected up to 2 days after inoculation.

Growth Phase

The perfusion and bleed were started when the cell concentration reached the experimental growth phase. The bleed/harvest rates ratio was 10/90(%). The harvest bottle was changed every day during the cultivation.

A pulse bleed strategy was applied as soon as the cell concentration was higher than the cell concentration target (6×10$^6$ cell/ml). Depending of the cell concentration, the pulse bleed size was varied from 0 to 20% of the working volume of the bioreactor.

The harvest rate was kept constant and checked daily.

Harvest

The cell culture was harvested from the tank to a blue cap flask. The culture was sterile filtered using a 0.22 µm filter. Approximately 1 L harvest was transferred into a sterile bag and frozen.

Results

The cell concentration remained stable at around 7-8×10$^6$ cell/ml.

The viability remained at around 85% and 90% for the cultivation. It resulted in a FIXa content of around 0.07%.

Regarding the GLA profile, Gla-11 and Gla-12 remained above 80%.

A high productivity and stable product was also obtained within continuous bleed.

Example 2

Example 2 describes the cultivation of Factor IX protein, performed using the process of the invention in an ATF perfusion device in large scale (>500 L). The process at large scale (Example 2) was performed using the same strain, media and general process steps as described above in Example 1. With respect to process parameters (i.e bioreactor parameters, operating conditions, etc.) these were also similar as described above in Example 1.

TABLE 2

Product quality data for Factor IX at lab & large scale for the previous process ("semi-continuous process") and the ATF process

| Bioreactor | Process | GLA11 + 12(%) | FIXa (%) |
|---|---|---|---|
| Lab scale | Semi-continuous process | 90 | ~0.03 |
| Large scale (>500 L) | Semi-continuous process | 90-93 | 0.02-0.06 |
| Lab scale | ATF | 80-90 | 0.06-0.13 |
| Large scale (>500 L) | ATF | 87-96 | 0.02-0.15 |

Results

Figure 2:
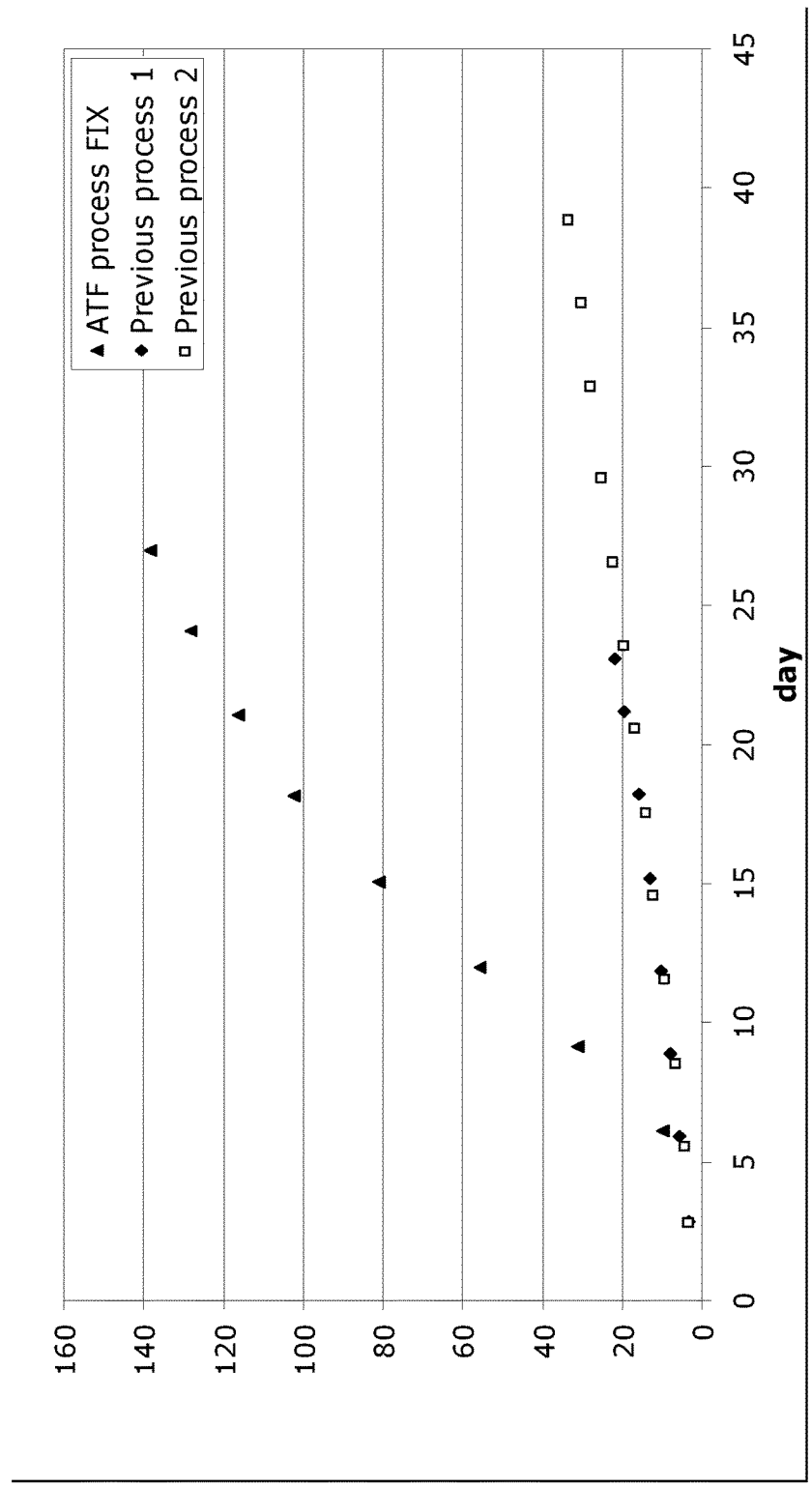
FIG. 2: Large scale (>500 L) yield comparison between previous process ("semi-continuous process") with ATF process for Factor IX (on a relative scale).
Figure 3:
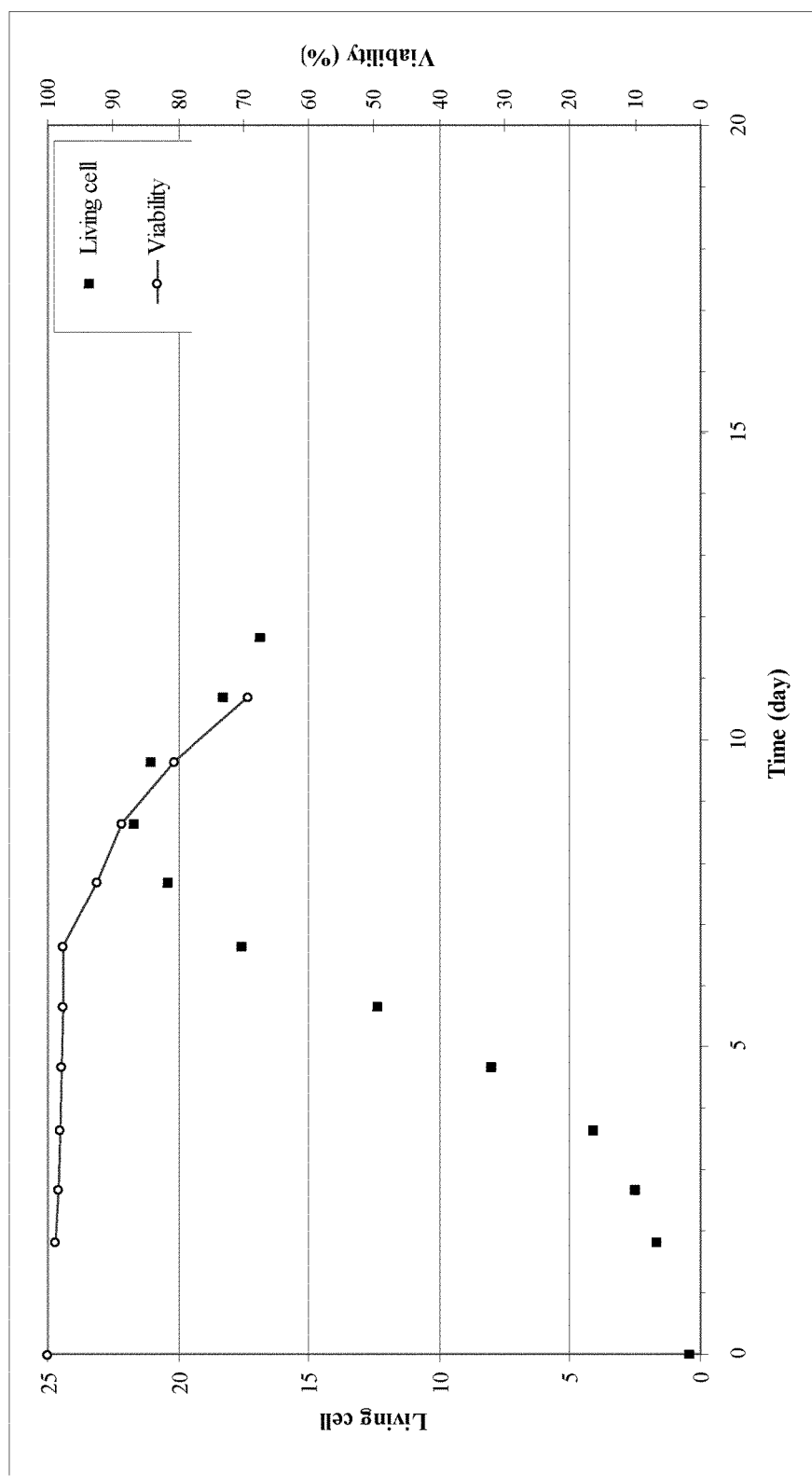
FIG. 3: Living cells concentration and viability for Factor IX cell lines at laboratory scale using ATF performed without bleed.
Figure 4:
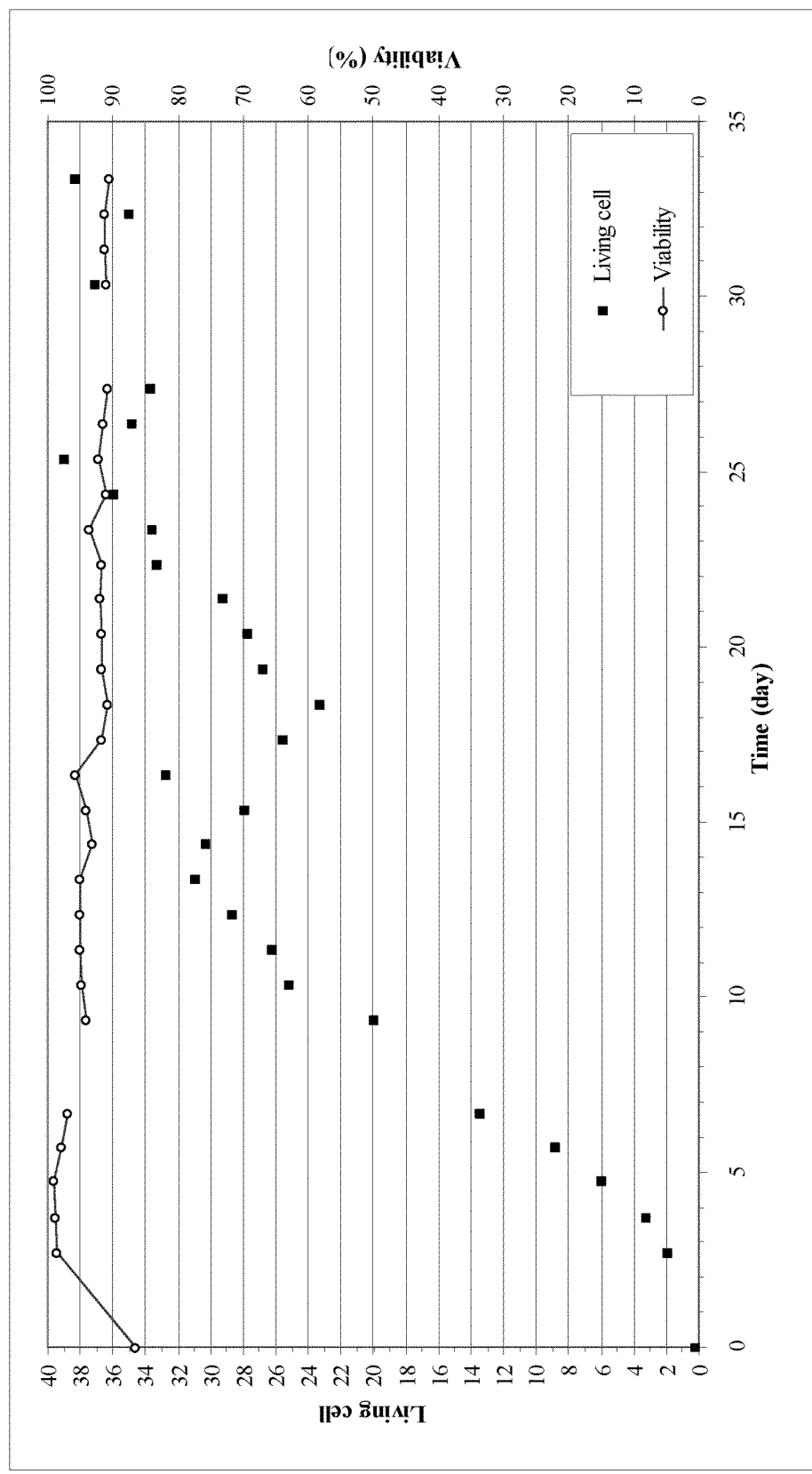
FIG. 4: Living cells concentration and viability for Factor VIII at laboratory scale using ATF.
Figure 5:
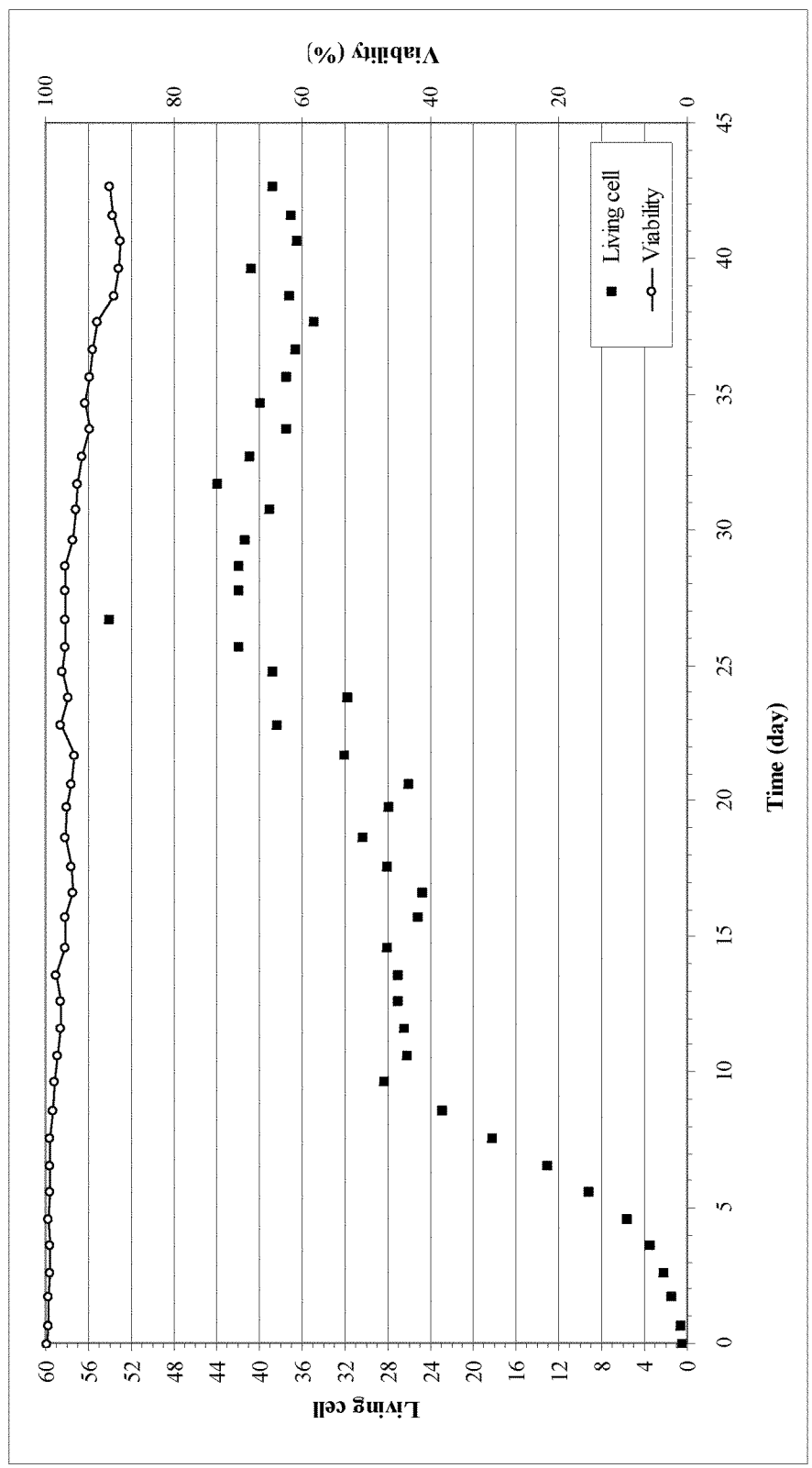
FIG. 5: Living cells concentration and viability for Factor VII at laboratory scale using ATF.

Table 2 shows that the quality of the produced Factor IX is maintained using the ATF process compared to previous process ("semi-continuous process"). However, the ATF process produces a much higher quantity/yield (as is shown in FIG. 2).

The invention claimed is:

1. A large-scale, continuous perfusion process for producing a haemostasis protein, comprising
providing a cell culture in suspension in a bioreactor, wherein the bioreactor is in fluid communication with a filter module, wherein the bioreactor volume is at least 500 L, and wherein the filter module mesh size is from about 0.1 µm to about 2.9 µm;
providing a dissolved oxygen concentration in the suspension of around 20% to 100%; and
flowing the cell culture suspension across the filter module in an alternating tangential flow, in order to separate haemostasis protein produced by the cell culture from the cells; and culturing the cells to a target cell density below $80 \times 10^6$ cells/ml.

2. The process of claim 1, wherein the haemostasis protein is Factor IX.

3. The process of claim 1, wherein the haemostasis protein is Factor VIII.

4. The process of claim 1, wherein the haemostasis protein is Factor VII.

5. The process of claim 1, wherein the perfusion rate is from 0.7 to 10 times the bioreactor volume per day.

6. The process of claim 1, wherein unfiltered cell culture suspension is removed at a rate of 0 to 50% of the bioreactor volume per day.

7. The process of claim 6, wherein unfiltered cell culture suspension is removed at a rate of 1 to 20% of the bioreactor volume per day.

8. The process according to claim 1, further comprising removing unfiltered cell culture suspension continuously.

9. The process according to claim 1, further comprising removing unfiltered cell culture suspension discontinuously.

10. The process according to claim 1, further comprising culturing the cells to a target cell density below $50 \times 10^6$ cells/ml.

11. The process according to claim 5, wherein the perfusion rate is from 0.9 to 4 times the bioreactor volume per day.

12. The process according to claim 1, wherein the cells in the cell suspension are Chinese Hamster Ovary (CHO) cells.

13. The process according to claim 12, wherein the cells in the cell suspension are CHO-KI cells.

14. The process according to claim 1, wherein the dissolved oxygen concentration is around 30 to 70%.

15. The process according to claim 14, wherein the dissolved oxygen concentration is around 45 to 55%.

16. The process according to claim 15, wherein the dissolved oxygen concentration is around 50%.

* * * * *